(12) United States Patent
Rezach et al.

(10) Patent No.: US 8,945,188 B2
(45) Date of Patent: Feb. 3, 2015

(54) SPINAL CORRECTION SYSTEM AND METHOD

(76) Inventors: William Alan Rezach, Atoka, TN (US); Charles Anthony Dickinson, Bartlett, TN (US); Rodney Ballard, Lakeland, TN (US)

( * ) Notice: Subject to any disclaimer, the term of this patent is extended or adjusted under 35 U.S.C. 154(b) by 114 days.

(21) Appl. No.: 13/441,100

(22) Filed: Apr. 6, 2012

(65) Prior Publication Data

US 2013/0268005 A1   Oct. 10, 2013

(51) Int. Cl.
*A61B 17/70* (2006.01)

(52) U.S. Cl.
USPC .......................... 606/263; 606/246

(58) Field of Classification Search
USPC ................. 606/246–278, 300–321, 330, 151
See application file for complete search history.

(56) References Cited

U.S. PATENT DOCUMENTS

| | | | |
|---|---|---|---|
| 5,534,002 A * | 7/1996 | Brumfield et al. ............ | 606/278 |
| 7,166,108 B2 | 1/2007 | Mazda et al. | |
| 7,481,828 B2 | 1/2009 | Mazda et al. | |
| 7,959,654 B2 | 6/2011 | Mazda et al. | |
| 8,172,843 B2 | 5/2012 | Baccelli et al. | |
| 8,323,318 B2 | 12/2012 | Baccelli et al. | |
| 8,323,319 B2 | 12/2012 | Mazda et al. | |
| 8,419,773 B2 * | 4/2013 | Biedermann et al. ........ | 606/260 |
| 2005/0131404 A1 | 6/2005 | Mazda et al. | |
| 2009/0138048 A1 | 5/2009 | Baccelli et al. | |
| 2009/0248077 A1 | 10/2009 | Johns | |
| 2009/0326585 A1 | 12/2009 | Baccelli et al. | |
| 2010/0249845 A1 | 9/2010 | Meunier et al. | |
| 2011/0034956 A1 | 2/2011 | Mazda et al. | |
| 2011/0112581 A1 | 5/2011 | Clement | |
| 2012/0027135 A1 | 2/2012 | Sgraja et al. | |

FOREIGN PATENT DOCUMENTS

| | | |
|---|---|---|
| EP | 2842724 A1 | 1/2004 |
| EP | 2890849 A1 | 3/2007 |
| EP | 2890850 A1 | 3/2007 |
| EP | 2890851 A1 | 3/2007 |
| EP | 1933743 A1 | 6/2008 |
| EP | 2052689 A1 | 4/2009 |
| EP | 2184023 A1 | 12/2010 |
| WO | 2009124062 A1 | 10/2009 |

\* cited by examiner

*Primary Examiner* — Mary Hoffman
*Assistant Examiner* — Christina Negrellirodrigue (57) ABSTRACT

An implant connector comprises a first surface defining a first cavity configured for disposal of a first implant. A second surface defines a second cavity configured for disposal of a coupling member. A third surface defines a third transverse cavity configured for disposal of a second implant. The third surface includes a projection configured to engage the second implant in a provisional locking orientation. Methods of use are disclosed.

6 Claims, 9 Drawing Sheets

SPINAL CORRECTION SYSTEM AND METHOD

TECHNICAL FIELD

The present disclosure generally relates to medical devices for the treatment of musculoskeletal disorders, and more particularly to a surgical system and method for correction of a spine disorder.

BACKGROUND

Spinal pathologies and disorders such as scoliosis and other curvature abnormalities, kyphosis, degenerative disc disease, disc herniation, osteoporosis, spondylolisthesis, stenosis, tumor, and fracture may result from factors including trauma, disease and degenerative conditions caused by injury and aging. Spinal disorders typically result in symptoms including deformity, pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes correction, fusion, fixation, discectomy, laminectomy and implantable prosthetics. Correction treatments used for positioning and alignment may employ implants, such as vertebral rods, bone screws and sub-laminar wire, for stabilization of a treated section of a spine. This disclosure describes an improvement over these prior art technologies.

SUMMARY

Accordingly, a spinal correction system is provided. In one embodiment, in accordance with the principles of the present disclosure, a spinal correction system is provided, which comprises an implant connector. The implant connector comprises a first surface defining a first cavity configured for disposal of a first implant. A second surface defines a second cavity configured for disposal of a coupling member. A third surface defines a third transverse cavity configured for disposal of a second implant. The third surface includes a projection configured to engage the second implant in a provisional locking orientation.

In one embodiment, the spinal correction system comprises a plurality of tethers including a first flexible tether. A spinal rod defines a central axis and includes an arcuate outer surface. A plurality of connectors include a first connector comprising a body including an outer surface and a first inner surface defining a first passageway extending through the body. The first passageway defines a first axis and is configured for disposal of the first flexible tether. The body further includes a second threaded inner surface defining a second passageway extending through the body. The second passageway defines a second axis disposed at an angular orientation relative to the first axis and is configured for disposal of a set screw. The set screw defines a central axis and a tapered tip including a concave surface. The body further includes a third surface defining a third passageway having an oblong cross section extending through the body. The third passageway defines a third axis disposed in a transverse orientation relative to the first axis and the second axis. The third passageway is configured for disposal of the spinal rod. The second passageway communicates with the third passageway such that the concave surface is engageable with the arcuate outer surface to translate the spinal rod laterally along the oblong cross section of the third passageway and the first passageway communicates with the third passageway such that the spinal rod is engageable with the first flexible tether for fixation therewith.

In one embodiment, a method for treating a spine disorder is provided. The method comprises the steps of: providing a first flexible implant; disposing the first flexible implant with a first vertebra; providing a first connector comprising: a first surface defining a first cavity, a second surface defining a second cavity configured for disposal of a coupling member, and a third surface defining a third transverse cavity and including a projection; providing a second implant; disposing the second implant with the third cavity such that the projection engages the second implant in a provisional locking orientation; disposing the first flexible implant with the first cavity; engaging the coupling member with the second implant to overcome the provisional locking orientation of the projection such that the second implant engages the first flexible implant for fixation therewith.

BRIEF DESCRIPTION OF THE DRAWINGS

The present disclosure will become more readily apparent from the specific description accompanied by the following drawings, in which.

Like reference numerals indicate similar parts throughout the figures.

DETAILED DESCRIPTION

The exemplary embodiments of a surgical system and related methods of use are discussed in terms of medical devices for the treatment of musculoskeletal disorders and more particularly, in terms of a spinal correction system. It is envisioned that the spinal correction system may be employed in applications for correction of deformities, such as scoliosis and kyphosis.

In one embodiment, the spinal correction system includes a closed connector. The closed connector includes a setscrew having a tip that forces a spinal rod laterally. The closed connector includes a hole for disposal of a tether. In one embodiment, the hole has a threaded diameter that increases grip strength with a tether. In one embodiment, the closed connector includes a bump that provides provisional locking with a vertebral rod. Upon application of sufficient torque to the setscrew, an axial force is applied to the vertebral rod to overcome a force resistance of the bump, which allows the rod to engage the tether for fixation therewith. This configuration reduces component assembly issues such as misalignment of parts and cumbersome handling. It is contemplated that the bump may be fabricated from metal or a compliant member, such as, for example, silicone, which resists final tightening in the provisional locking configuration.

In one embodiment, the spinal correction system includes an open connector. In one embodiment, the tether can be cylindrical having a diameter. In one embodiment, the tether can have a flat configuration having a thickness and allowing ease of passing the tether under a lamina of vertebrae. It is contemplated that the open connector includes a bump or provisional tightening feature to prevent a rod from contacting the tether until final tightening.

In one embodiment, the spinal correction system is employed with a procedure for placing multiple tethers. The multiple tethers are placed one at a time with each vertebral level. Each tether has a loop on one end. After placing the tether under lamina/transverse process of a vertebral level, the tether is placed through a loop for attachment to the vertebral level, similar to a lasso or stringer attachment configuration. The connector is mounted onto the rod and provisionally locked to maintain the connector from sliding, spinning and/or disengaging from the rod. The tethers are then passed through the connector.

It is contemplated that one or all of the components of the spinal correction system may be disposable, peel-pack, prepacked sterile devices. One or all of the components of the system may be reusable. The system may be configured as a kit with multiple sized and configured components.

It is envisioned that the present disclosure may be employed to treat spinal disorders such as, for example, degenerative disc disease, disc herniation, osteoporosis, spondylolisthesis, stenosis, scoliosis and other curvature abnormalities, kyphosis, tumor and fractures. It is contemplated that the present disclosure may be employed with other osteal and bone related applications, including those associated with diagnostics and therapeutics. It is further contemplated that the disclosed system may be alternatively employed in a surgical treatment with a patient in a prone or supine position, and/or employ various surgical approaches to the spine, including anterior, posterior, posterior mid-line, direct lateral, postero-lateral, and/or antero-lateral approaches, and in other body regions. The present disclosure may also be alternatively employed with procedures for treating the lumbar, cervical, thoracic and pelvic regions of a spinal column. The system and methods of the present disclosure may also be used on animals, bone models and other non-living substrates, such as, for example, in training, testing and demonstration.

The present disclosure may be understood more readily by reference to the following detailed description of the disclosure taken in connection with the accompanying drawing figures, which form a part of this disclosure. It is to be understood that this disclosure is not limited to the specific devices, methods, conditions or parameters described and/or shown herein, and that the terminology used herein is for the purpose of describing particular embodiments by way of example only and is not intended to be limiting of the claimed disclosure. Also, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

Further, as used in the specification and including the appended claims, "treating" or "treatment" of a disease or condition refers to performing a procedure that may include administering one or more drugs to a patient (human, normal or otherwise or other mammal), in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, ligaments, tendons, cartilage and/or bone unless specifically referred to otherwise.

The following discussion includes a description of a spinal correction system in accordance with the principles of the present disclosure. Alternate embodiments are also disclosed. Reference will now be made in detail to the exemplary embodiments of the present disclosure, which are illustrated in the accompanying figures. Turning now to FIGS. 1-6, there is illustrated components of a system, such as, for example, a spinal correction system 20 in accordance with the principles of the present disclosure.

The components of spinal correction system 20 can be fabricated from biologically acceptable materials suitable for medical applications, including metals, synthetic polymers, ceramics, bone material, tissue and/or their composites, depending on the particular application and/or preference of a medical practitioner. For example, the components of spinal correction system 20, individually or collectively, can be fabricated from materials such as stainless steel alloys, commercially pure titanium, titanium alloys, Grade 5 titanium, super-elastic titanium alloys, cobalt-chrome alloys, stainless steel alloys, superelastic metallic alloys (e.g., Nitinol, super elasto-plastic metals, such as GUM METAL® manufactured by Toyota Material Incorporated of Japan), ceramics and composites thereof such as calcium phosphate (e.g., SKEL-ITE™ manufactured by Biologix Inc.), thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tri-calcium phosphate (TCP), hydroxyapatite (HA)-TCP, calcium sulfate, or other resorbable polymers such as polyaetide, polyglycolide, polytyrosine carbonate, polycaroplaetohe and their combinations. Various components of system 20 may have material composites, including the above materials, to achieve various desired characteristics such as strength, rigidity, elasticity, compliance, biomechanical performance, durability and radiolucency or imaging preference. The components of system 20, individually or collectively, may also be fabricated from a heterogeneous material such as a combination of two or more of the above-described materials. The components of system 20 may be monolithically formed, integrally connected or include fastening elements and/or instruments, as described herein.

System 20 is employed, for example, with an open, mini-open or minimally invasive including percutaneous surgical technique to attach a longitudinal element to a spine that has a spinal disorder. In one embodiment, the longitudinal element may be affixed to a selected section of the spine and/or other anatomy while allowing for growth and adjustments to a concave side of a plurality of vertebrae for a correction treatment to treat various spine pathologies, such as, for example, adolescent idiopathic scoliosis and Scheuermann's kyphosis.

Figure 7:
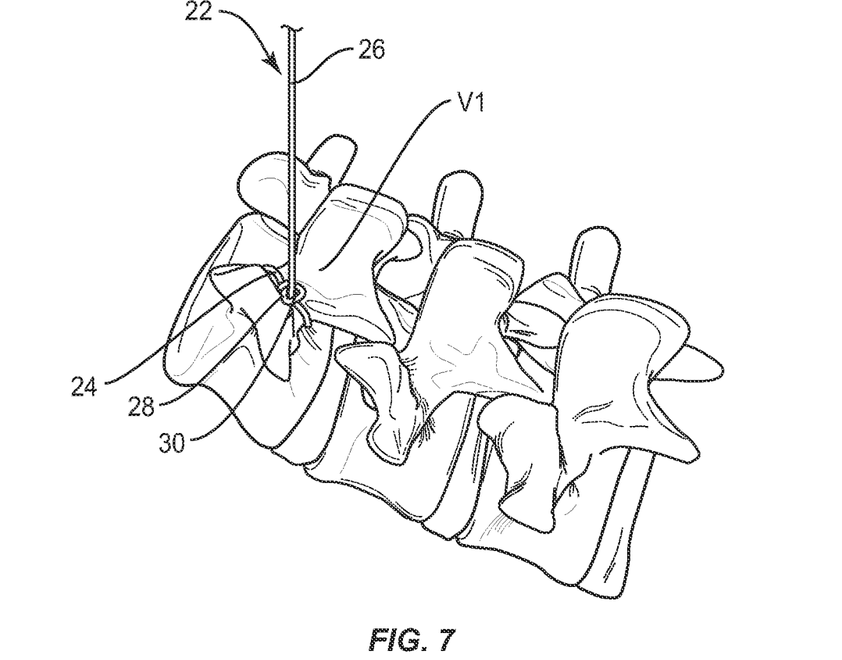
FIG. 7 is a perspective view of a component of the system shown in FIG. 1 disposed with a vertebra of a spine.
Figure 8:
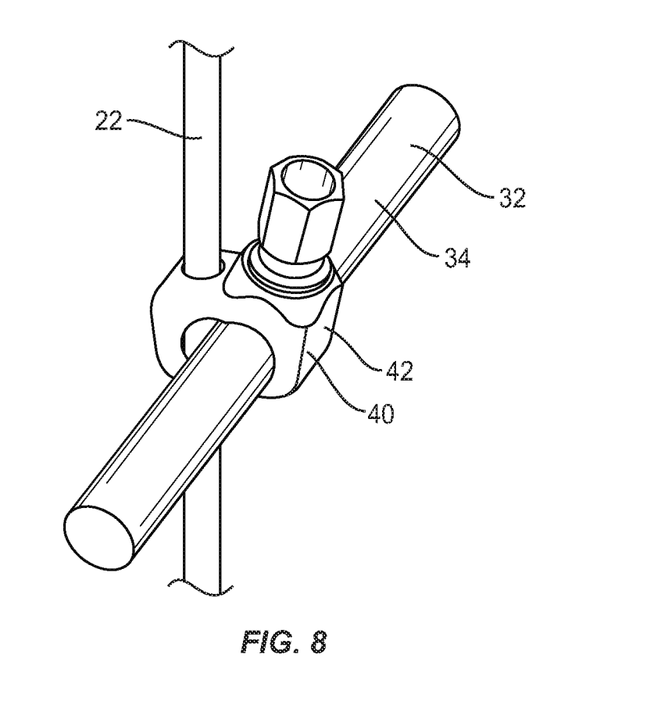
FIG. 8 is a perspective view of one embodiment of the spinal correction system in accordance with the principles of the present disclosure.

Spinal correction system 20 includes a first implant, such as, for example, a tether 22 (FIGS. 7 and 8). Tether 22 is a flexible longitudinal element that extends between a first end 24 and a second free end 26. First end 24 includes a loop 28 defining a cavity 30. Cavity 30 is configured for disposal of a portion of tether 22 such that tether 22 can be tensioned about a targeted portion of an anatomy of a body for attachment of tether 22 with the targeted portion of the anatomy, as will be described. It is contemplated that tether 22 may manipulated manually and/or with a surgical tensioning instrument. It is further contemplated that the targeted portion of the anatomy may include a lamina, transverse process and/or pedicle regions of a vertebral level. It is envisioned that spinal correction system 20 may include one or a plurality of tethers 22, each tether being configured for disposal about a single and separate vertebral level. It is further envisioned that a single vertebral level may include one or a plurality of tethers 22.

Tether 22 has a flexible configuration and may be fabricated from materials, such as, for example, fabric, silicone, polyurethane, silicone-polyurethane copolymers, polymeric rubbers, polyolefin rubbers, elastomers, rubbers, thermoplastic elastomers, thermoset elastomers and elastomeric composites. In one embodiment, the flexibility of tether 22 includes movement in a lateral or side to side direction and prevents expanding and/or extension in an axial direction upon tensioning of first end 24 and attachment with a targeted portion of the anatomy. It is envisioned that all or only a portion of tether 22 may have a semi-rigid, rigid or elastic configuration, and/or have elastic properties such that tether 22 provides a selective amount of expansion and/or extension in an axial direction. It is further envisioned that tether 22 may be compressible in an axial direction. Tether 22 can include a plurality of separately attachable or connectable portions or sections, such as bands or loops, or may be monolithically formed as a single continuous element.

Tether 22 can have a uniform thickness/diameter. It is envisioned that tether 22 may have various surface configurations, such as, for example, smooth and/or surface configurations to enhance fixation, such as, for example, rough, arcuate, undulating, porous, semi-porous, dimpled, polished and/or textured according to the requirements of a particular application. It is contemplated that the thickness defined by tether 22 may be uniformly increasing or decreasing, or have alternate diameter dimensions along its length. It is further contemplated that tether 22 may have various cross section configurations, such as, for example, oval, oblong, triangular, rectangular, square, polygonal, irregular, uniform, non-uniform, variable and/or tapered. It is contemplated that the surface of tether 22 may include engaging structures, such as, for example, barbs, raised elements and/or spikes to facilitate engagement with tissue of the targeted anatomy.

It is contemplated that tether 22 may have various lengths, according to the requirements of a particular application. It is further contemplated that tether 22 may be braided, such as a rope, or include a plurality elongated elements to provide a predetermined force resistance. It is envisioned that tether 22 may be made from autograft and/or allograft, and be configured for resorbable or degradable applications. In one embodiment, the first implant is a cadaver tendon. In one embodiment, the first implant is a tendon that may be harvested, for example, from a patient or donor. It is contemplated that a tendon harvested from a patient may be affixed in remote locations with the patient's body.

Spinal correction system 20 includes a second implant, such as, for example, a spinal rod 32 having a cylindrical cross section configuration. Spinal rod 32 defines a central axis c1 and includes an arcuate outer surface 34. Spinal rod 32 extends between a first end 36 and a second end 38. It is envisioned that spinal correction system 20 may include one or a plurality of spinal rods 32, which may be relatively disposed in a side by side, irregular, uniform, non-uniform, offset and/or staggered orientation or arrangement.

It is contemplated that spinal rod 32 can have a uniform thickness/diameter. It is envisioned that spinal rod 32 may have various surface configurations, such as, for example, rough, threaded for connection with surgical instruments, arcuate, undulating, dimpled, polished and/or textured according to the requirements of a particular application. It is contemplated that the thickness defined by spinal rod 32 may be uniformly increasing or decreasing, or have alternate diameter dimensions along its length. It is further contemplated that spinal rod 32 may have various cross section configurations, such as, for example, oval, oblong, triangular, rectangular, square, polygonal, irregular, uniform, non-uniform, variable and/or tapered. It is contemplated that spinal rod 32 may have various lengths, according to the requirements of a particular application.

Spinal correction system 20 includes an implant connector, such as, for example, a connector 40. Connector 40 includes a body 42 having an angled configuration. Body 42 includes an outer surface 44. It is contemplated that spinal correction system 20 may include one or a plurality of implant connectors spaced apart and disposed along spinal rod 32, as will be described, which may be relatively disposed in a side by side, irregular, uniform, non-uniform, offset and/or staggered orientation or arrangement, along one or a plurality of spinal rods.

It is contemplated that all or only a portion of body 42 can have a uniform thickness/diameter. It is envisioned that outer surface 44 may have various surface configurations, such as, for example, rough, threaded for connection with surgical instruments, arcuate, undulating, dimpled, polished and/or textured according to the requirements of a particular application. It is contemplated that the thickness defined by body 42 may be uniformly increasing or decreasing, or have alternate diameter dimensions along its length. It is further contemplated that all or only a portion of body 42 may have various cross section configurations, such as, for example, oval, oblong, triangular, rectangular, square, polygonal, irregular, uniform, non-uniform, variable and/or tapered.

Body 42 includes a first inner surface 46 that defines a first cavity, such as, for example, a first passageway 48. First passageway 48 is substantially cylindrical and extends through body 42 from a first face 50 of outer surface 44 to a second face 52 of outer surface 44. First inner surface 46 includes a gripping element, such as, for example, an internal thread form 54 configured to enhance fixation with tether 22, as will be described, according to the requirements of a particular application. It is contemplated that thread form 54 may include a single thread turn or a plurality of discrete threads. It is further contemplated that other gripping elements may be located on first inner surface 46, such as, for example, a nail configuration, barbs, expanding elements, raised elements and/or spikes to facilitate engagement of first inner surface 46 with tether 22. It is envisioned that first inner surface 46 may include one or a plurality of gripping elements.

First passageway 48 defines a first axis a1 and is configured for disposal of tether 22. First passageway 48 facilitates movement of tether 22 therealong and fixation with first inner surface 46 upon tensioning of tether 22, according to the requirements of a particular application, for fixation with a targeted portion of the anatomy.

It is envisioned that all or only a portion of first passageway 48 may have alternate cross section configurations, such as, for example, oval, oblong, triangular, square, polygonal, irregular, uniform, non-uniform, offset, staggered, undulating, arcuate, variable and/or tapered. It is contemplated that first passageway 48 may include one or a plurality of openings that may extend through body 42 to outer surface 44. It is contemplated that all or only a portion of first inner surface 46 may have alternate surface configurations to enhance fixation with tether 22, including or alternative to a gripping element, such as, for example, rough, arcuate, undulating, mesh, porous, semi-porous, dimpled and/or textured according to the requirements of a particular application.

Body 42 includes a second inner surface 56 that defines a second cavity, such as, for example, a second passageway 58. Second passageway 58 is substantially cylindrical and extends through body 42 from a third face 60 of outer surface 44 to a third interior cavity, as will be discussed. Second inner surface 56 includes an internal thread form 62 configured for engagement with a coupling member, as will be discussed. It is contemplated that thread form 62 may include a single thread turn or a plurality of discrete threads.

It is envisioned that all or only a portion of second passageway 58 may have alternate cross section configurations, such as, for example, oval, oblong, triangular, square, polygonal, irregular, uniform, non-uniform, offset, staggered, undulating, arcuate, variable and/or tapered. It is contemplated that second passageway 58 may include one or a plurality of openings that may extend through body 42 to outer surface 44.

Second passageway 58 defines a second axis, such as, for example, axis a2 disposed at an angular orientation, such as, for example, an angle α relative to axis a1. It is envisioned that all or only a portion of axis a2 corresponding to second passageway 58 may be disposed at alternate orientations, relative to axis a1 corresponding to second passageway 48, such as, for example, transverse, perpendicular and/or other angular orientations such as acute or obtuse and/or may be offset or staggered.

Second passageway 58 is configured for disposal of a coupling member, such as, for example, a set screw 64. Set screw 64 defines a central axis c2, which is disposed in a co-axial alignment with axis a2 upon disposal of set screw 64 with second passageway 58. Set screw 64 has a tubular body that includes an outer surface 66 and an inner surface 68.

Outer surface 66 includes a thread form 70 formed circumferentially about a distal end 72. Thread form 70 threadably engages thread form 62 such that application of torque to set screw 64 causes set screw 64 to translate axially along axis a2. Inner surface 68 is configured to have a wall shear strength such that set screw 64 shears at a pre-determined amount of torque. It is envisioned that set screw 64 may be disposed with inner surface 68 in alternate fixation configurations, such as, for example, friction fit, pressure fit, locking protrusion/recess and/or locking keyway. It is further envisioned that set screw 64 may be a non-breakoff setscrew that is not configured to shear at a pre-determined amount of torque. In one embodiment, set screw 64 may includes internal and/or external drive features.

Set screw 64 includes a tapered tip 76 including a concave outer surface 78 disposed circumferentially thereabout. Concave surface 78 is configured for engagement with outer surface 34 to drive spinal rod 32 into engagement with tether 22, as will be described. In one embodiment, set screw 64 may include a tapered or conical tip.

Body 42 includes a third inner surface 80 that defines a third cavity, such as, for example, a third passageway 82. Third passageway 82 has an oblong configuration and extends through body 42 from a side face 84 of outer surface 44 to a side face 86 of outer surface 44. It is envisioned that all or only a portion of third passageway 82 may have alternate cross section configurations, such as, for example, oval, cylindrical, triangular, square, polygonal, irregular, uniform, non-uniform, offset, staggered, undulating, arcuate, variable and/or tapered. It is contemplated that third passageway 82 may include one or a plurality of openings that may extend through body 42 to outer surface 44.

Third passageway 82 defines a third axis, such as, for example, axis a3 disposed in a transverse orientation relative to axis a1 and axis a2. It is envisioned that all or only a portion of axis a3 may be disposed at alternate orientations, relative to axis a1 and/or axis a2, such as, for example, transverse, perpendicular and/or other angular orientations such as acute or obtuse and/or may be offset or staggered. First passageway 48 intersects with third passageway 82 such that first passageway 48 communicates with third passageway 82. Second passageway 58 intersects with third passageway 82 such that second passageway 58 communicates with third passageway 82.

Third passageway 82 is configured for disposal of spinal rod 32 such that connector 40 can be mounted with spinal rod 32, according to the requirements of a particular application. Third inner surface 80 includes a projection 88 configured to engage spinal rod 32 in a provisional locking orientation. Projection 88 is employed as a provisional and/or working feature to temporarily support spinal rod 32 with connector 40 during a corrective procedure. The configuration of projection 88 temporarily stabilizes and fixes the components of spinal correction system 20 in an orientation, prevents spinal rod 32 from contacting tether 22 until final tightening and/or maintains connector 40 from sliding, spinning and/or disengaging from spinal rod 32, according to the requirements of a particular application. In one embodiment, projection 88 has a bump or dimple configuration. In one embodiment, projection 88 is a ridge or edge that extends across a portion of third inner surface 80. In one embodiment, inner surface 80 has a uniform and even surface configuration, for example, not including a projection 88 within passageway 82.

In operation, spinal rod 32 is disposed in a first configuration (FIGS. 3-5) such that projection 88 engages spinal rod 32 with a resistance to maintain a provisional locking orientation between connector 40 and spinal rod 32, as described above. Second passageway 58 communicates with third passageway 82 such that concave surface 78 is engageable with arcuate outer surface 34. A driving tool engages and applies a torque to set screw 64 and causes set screw 64 to translate axially along axis a2, as shown by arrow A in FIGS. 5 and 6. As set screw 64 translates, concave surface 78 engages outer surface 34.

Figure 1:
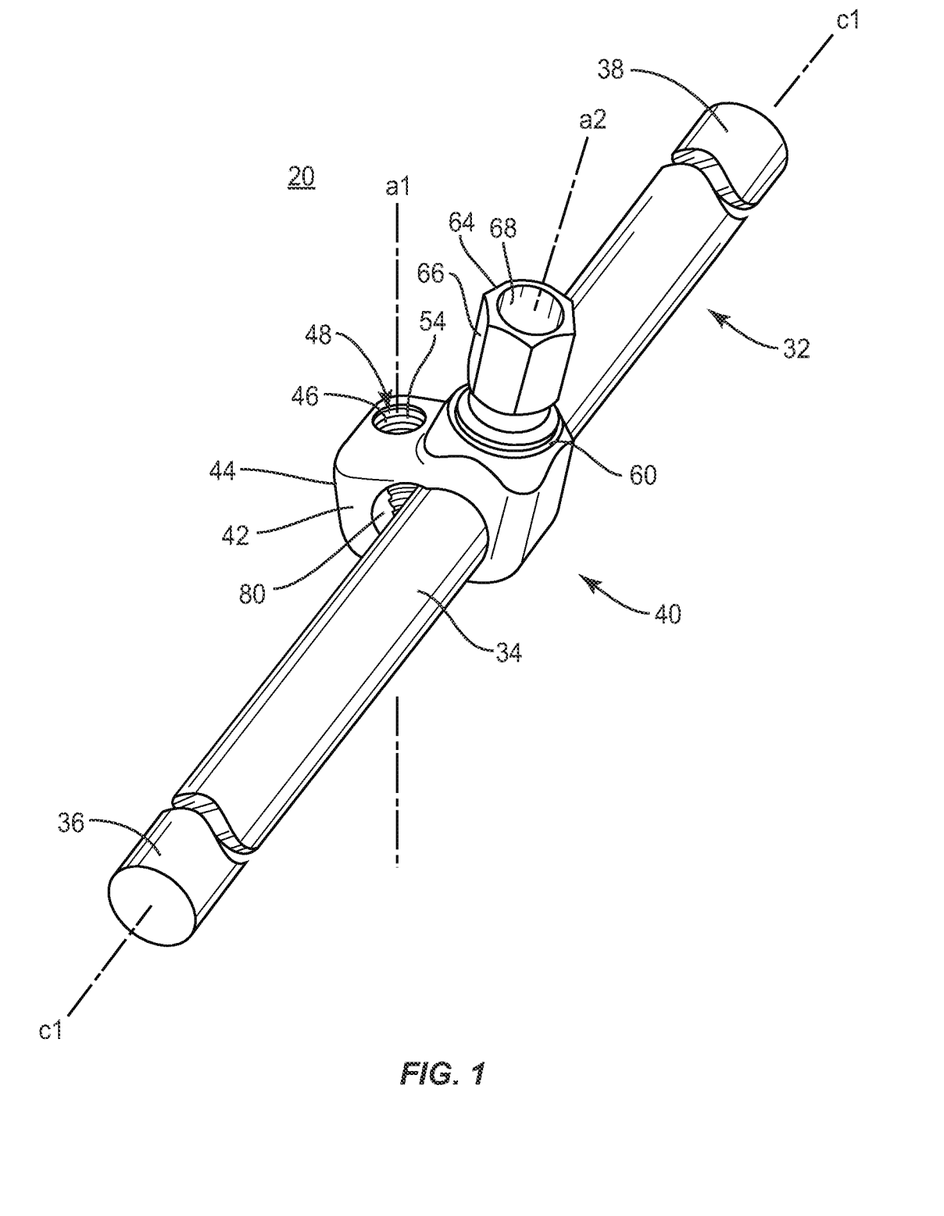
FIG. 1 is a perspective view of one particular embodiment of components of a spinal correction system in accordance with the principles of the present disclosure.
Figures 2, 3, 4:
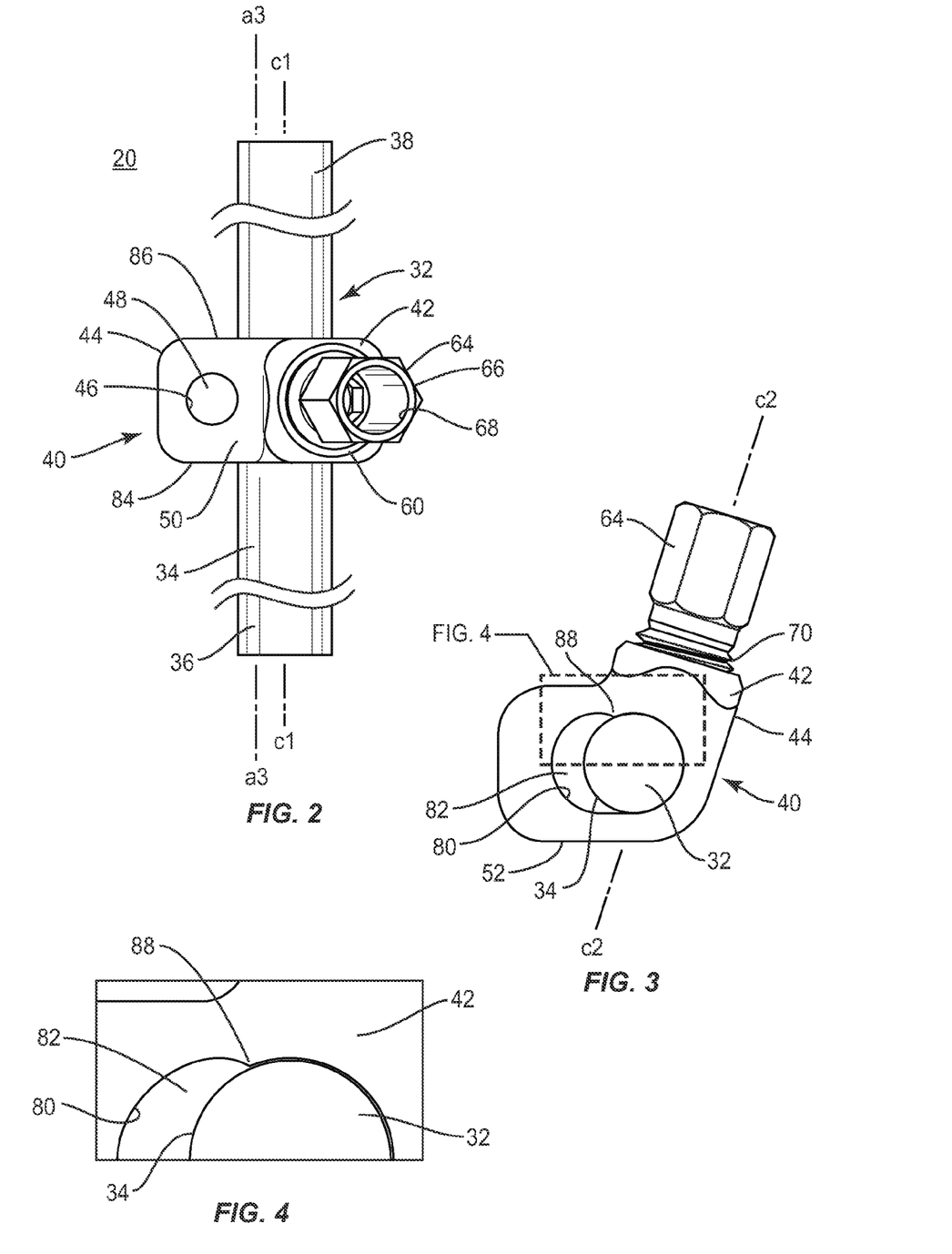
FIG. 2 is a side view of the components of the system shown in FIG. 1.
FIG. 3 is a side view of the components of the system shown in FIG. 1.
FIG. 4 is an enlarged detail view as identified in FIG. 3.
Figure 5:
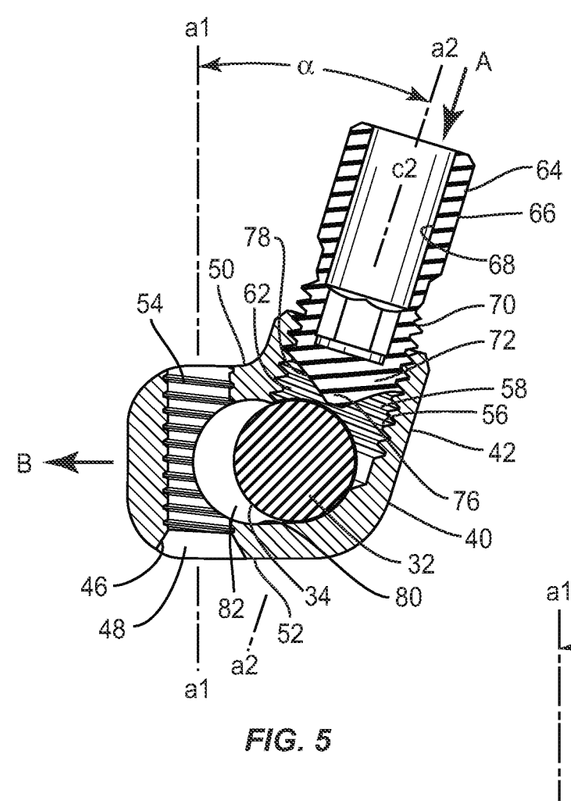
FIG. 5 is a side cross-section view of the components of the system shown in FIG. 1.
Figure 6:
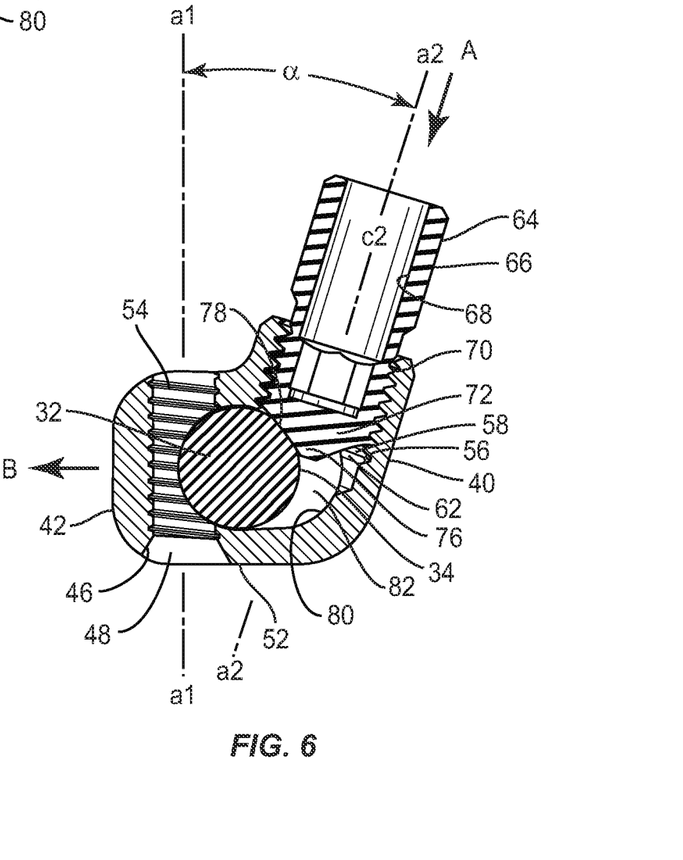
FIG. 6 is a side cross-section view of the components of the system shown in FIG. 1.

As concave surface 78 engages outer surface 34, such engagement overcomes the resistance of projection 88 to permit axial translation of spinal rod 32. This configuration causes spinal rod 32 to translate laterally, in the direction shown by arrow B in FIGS. 5 and 6, along the oblong cross section of third passageway 82. First passageway 48 communicates with third passageway 82 such that spinal rod 32 is engageable with tether 22 (FIG. 8). As such, spinal rod 32 is movable from the first configuration to a second configuration, as shown in FIG. 6, such that spinal rod 32 translates into engagement with tether 22 for fixation therewith.

In assembly, operation and use, a surgical system including spinal correction system 20, similar to that described above, is employed with a surgical procedure, such as, for example, a correction treatment to treat adolescent idiopathic scoliosis and/or Scheuermann's kyphosis of a spine. It is contemplated that one or all of the components of spinal correction system 20 can be delivered or implanted as a pre-assembled device or can be assembled in situ. The system including spinal correction system 20 may be completely or partially revised, removed or replaced.

For example, spinal correction system 20 can be employed with a surgical correction treatment of an applicable condition or injury of an affected section of a spinal column and adjacent areas within a body, such as, for example, at least a first vertebra V1, a second vertebra V2, a third vertebra V3 and a fourth vertebra V4 of vertebrae V. It is envisioned that spinal correction system 20 may be employed with one or a plurality of vertebrae.

In use, to treat a selected section of vertebrae V, a medical practitioner obtains access to a surgical site including vertebrae V in any appropriate manner, such as through incision and retraction of tissues. It is envisioned that the spinal correction system can be used in any existing surgical method or technique including open surgery, mini-open surgery, minimally invasive surgery and percutaneous surgical implantation, whereby vertebrae V is accessed through a mini-incision, or sleeve that provides a protected passageway to the area. Once access to the surgical site is obtained, the particular surgical procedure can be performed for treating the spine disorder.

An incision is made in the body of a patient and a cutting instrument (not shown) creates a surgical pathway for implantation of components of spinal correction system 20. A preparation instrument (not shown) can be employed to prepare tissue surfaces of vertebrae V, as well as for aspiration and irrigation of a surgical region according to the requirements of a particular surgical application.

Figure 9:
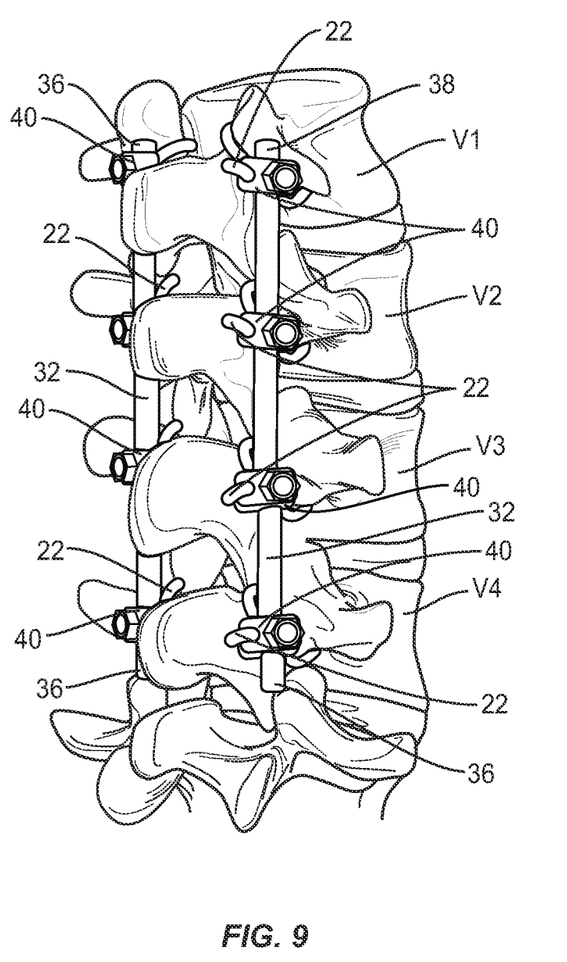
FIG. 9 is a perspective view of one embodiment of the spinal correction system in accordance with the principles of the present disclosure disposed with vertebrae of the spine.
Figure 10:
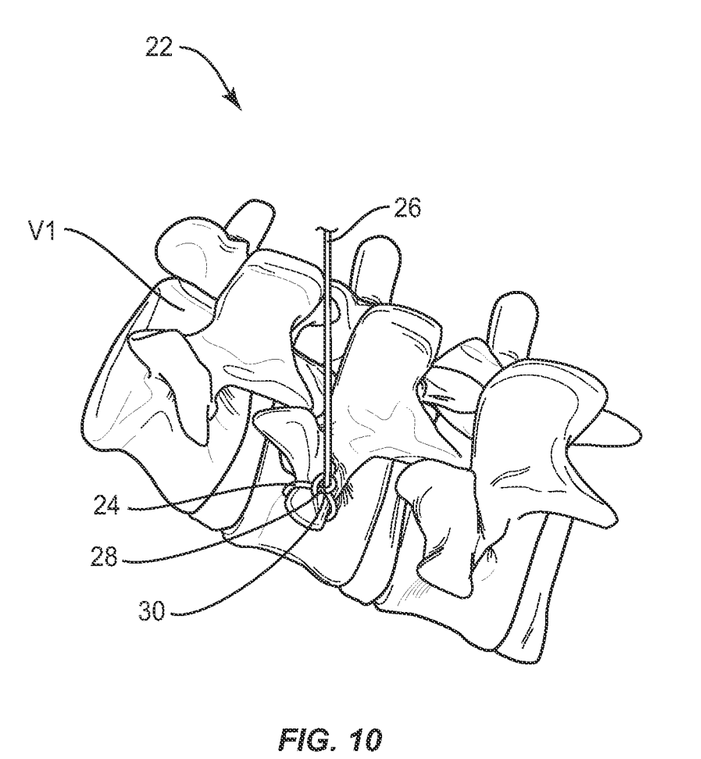
FIG. 10 is a perspective view of a component of the system shown in FIG. 1 disposed with a vertebra of a spine.
Figure 11:
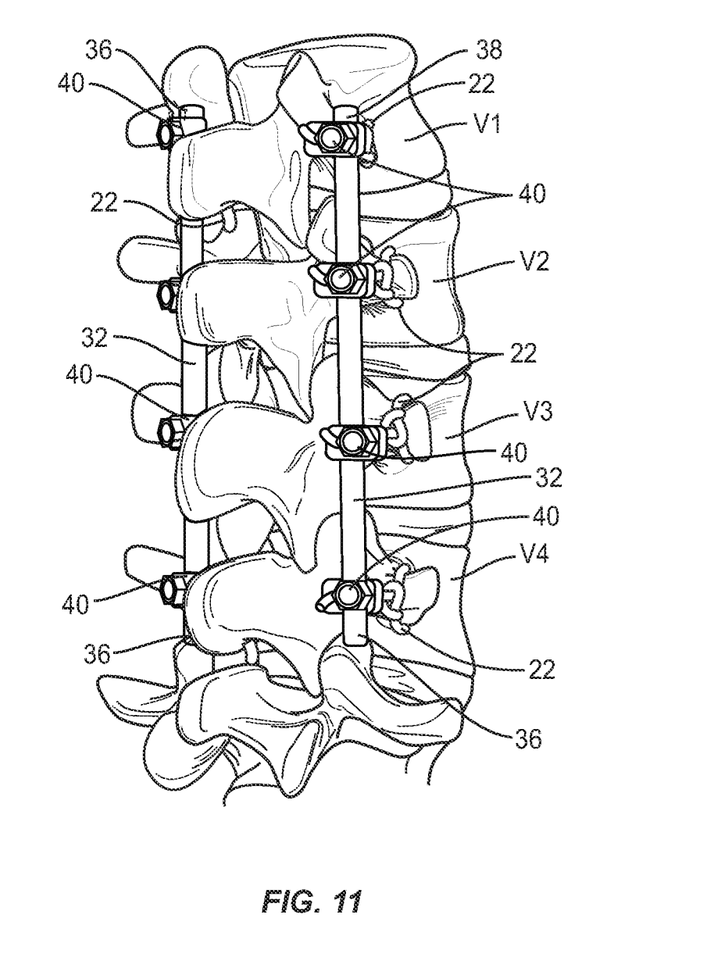
FIG. 11 is a perspective view of one embodiment of the spinal correction system in accordance with the principles of the present disclosure disposed with vertebrae of the spine.
Figures 12, 13:
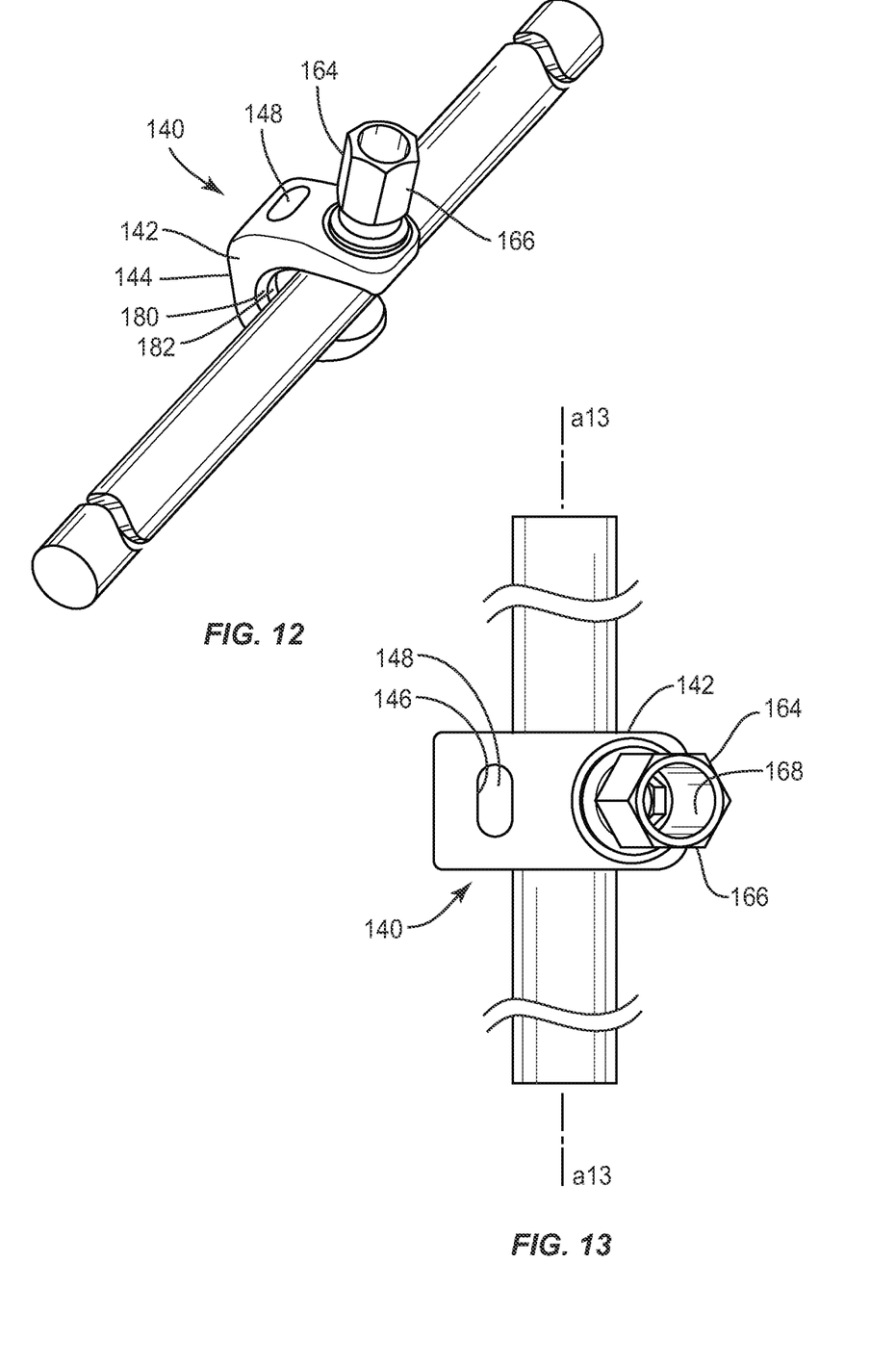
FIG. 12 is a perspective view of one embodiment of components of a spinal correction system in accordance with the principles of the present disclosure.
FIG. 13 is a side view of the components of the system shown in FIG. 12.
Figure 14:
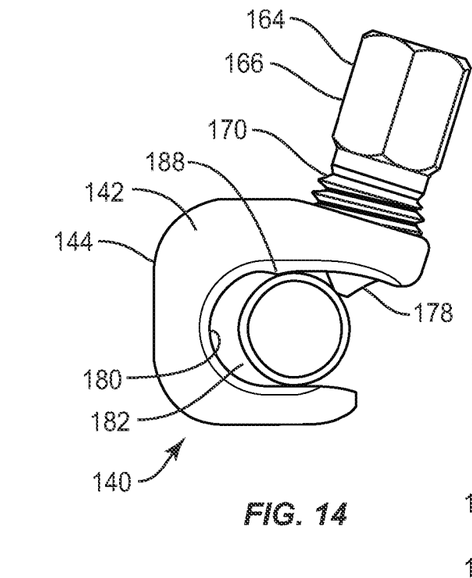
FIG. 14 is a side view of the components of the system shown in FIG. 12.
Figure 15:
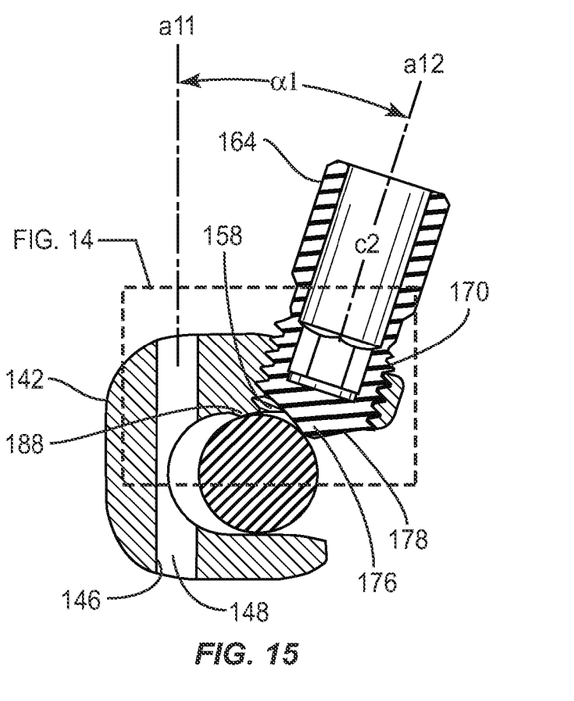
FIG. 15 is a side cross-section view of the components of the system shown in FIG. 12.
Figure 16:
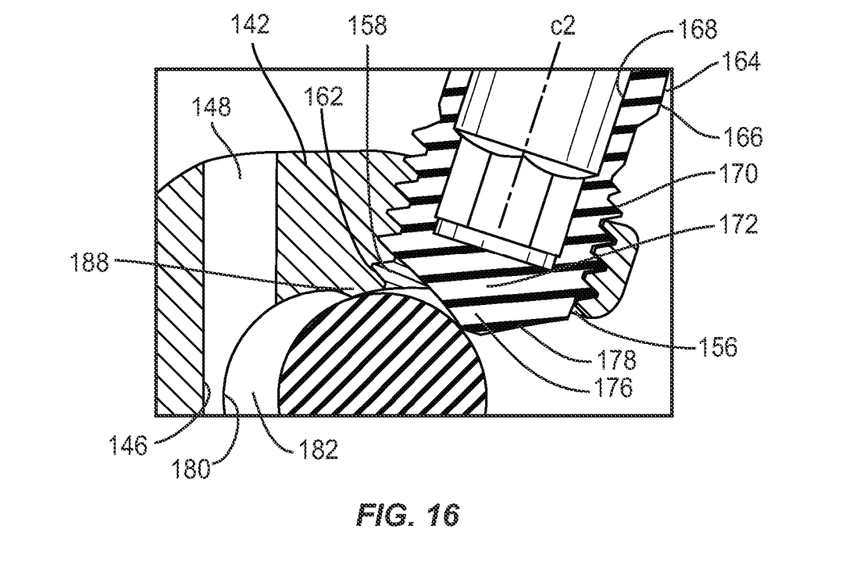
FIG. 16 is an enlarged detail view as identified in FIG. 15.

Referring to FIGS. 7-9, a first tether 22 is delivered along the surgical pathway to a surgical site adjacent vertebrae V. First tether 22 is disposed with vertebra V1. In one embodiment, as shown in FIGS. 7-9, loop 28 is disposed about a lamina of vertebra V1 by passing first end 24 continuously about the lamina. Second free end 26 is passed through cavity 30 and drawn away from vertebra V1. Second free end 26 is drawn and/or tensioned to tighten first end 24 with the outer surface of the lamina in a loop knot. This configuration fixes and/or attaches first end 24 with the lamina. In one embodiment, as shown in FIGS. 10-11, loop 28 is disposed about a transverse process of vertebra V1 by passing first end 24 continuously about the transverse process. Second free end 26 is passed through cavity 30 and drawn away from vertebra V1. Second free end 26 is drawn and/or tensioned to tighten first end 24 with the outer surface of the transverse process in a loop knot. This configuration fixes and/or attaches first end 24 with the transverse process and/or lamina.

A first spinal rod 32 is disposed with first connector 40 such that projection 88 engages first spinal rod 32 in a provisional locking orientation, as described above. It is contemplated that first connector 40 and first spinal rod 32 can be delivered or implanted as pre-assembled components or can be assembled in situ. First connector 40 and first spinal rod 32 are delivered along the surgical pathway to the surgical site adjacent vertebrae V.

First tether 22 is slidably drawn or threaded through first passageway 48, as shown in FIG. 8, to dispose first connector 40 and first spinal rod 32 at the surgical site and in contact with vertebra V1. First spinal rod 32 is disposed in a first configuration (FIG. 5), as described above. A driving tool engages and applies a torque to set screw 64 and causes set screw 64 to translate axially along axis a2 (as shown by arrow A in FIGS. 5 and 6). As set screw 64 translates, concave surface 78 engages outer surface 34.

As concave surface 78 engages outer surface 34, such engagement overcomes the resistance of projection 88 to permit axial translation of first spinal rod 32. This configuration causes first spinal rod 32 to translate laterally (as shown by arrow B in FIGS. 5 and 6) along the oblong cross section of third passageway 82. First spinal rod 32 is movable from the first configuration to a second configuration (FIG. 6) such that first spinal rod 32 translates into engagement with first tether 22 for fixation therewith.

Spinal correction system 20 includes a second connector 40, similar to first connector 40, spaced apart from the first connector 40 along spinal rod 32, as shown in FIG. 9. Second connector 40 is configured for disposal of a second flexible tether 22, separate from the first flexible tether 22, which is tensioned with vertebra V2. Spinal correction system 20 includes a third connector 40 and a fourth connector 40, similar to first connector 40, which are configured for disposal of tethers 22 tensioned with vertebrae V3, V4, respectively. First spinal rod 32 is disposed with vertebrae V along a first side of the spinous process. Spinal correction system 20 includes a second spinal rod 32 mounted with a plurality of connectors 40 and tethers 22 along a second side of the spinous process. The spinal rods 32 are mounted with vertebrae V in a side by side orientation according to the requirements of a particular application. As such, spinal correction system 20 stabilizes vertebrae V and affects growth for a correction treatment to treat various spine pathologies.

Upon completion of the procedure, the surgical instruments and assemblies are removed and the incision is closed. The system including spinal correction system 20 can be made of radiolucent materials such as polymers. Radiomarkers may be included for identification under x-ray, fluoroscopy, CT or other imaging techniques. It is envisioned that the use of microsurgical and image guided technologies may be employed to access, view and repair spinal deterioration or damage, with the aid of the system including spinal correction system 20.

It is contemplated that the components of the system including spinal correction system 20 may be employed to treat progressive idiopathic scoliosis with or without sagittal deformity in either infantile or juvenile patients, including but not limited to prepubescent children, adolescents from 10-12 years old with continued growth potential, and/or older children whose growth spurt is late or who otherwise retain growth potential. It is further contemplated that the components of spinal correction system 20 and related methods may be used to prevent or minimize curve progression in individuals of various ages.

In one embodiment, as shown in FIGS. 12-16, spinal correction system 20, similar to the apparatus and methods described above with regard to FIGS. 1-11, includes an implant connector, such as, for example, a connector 140. Connector 140 includes a body 142 having a C-shaped configuration. Body 142 includes an outer surface 144.

Body 142 includes a first inner surface 146 that defines a first cavity, such as, for example, a first passageway 148. First passageway 148 has an oblong cross section configuration and extends through body 142. First passageway 148 defines a first axis a11 and is configured for disposal of tether 22, as described above. First passageway 148 facilitates movement of tether 22 therealong and fixation with first inner surface 146 upon tensioning of tether 22, according to the requirements of a particular application, for fixation with a targeted portion of the anatomy.

Body 142 includes a second inner surface 156 that defines a second cavity, such as, for example, a second passageway 158. Second passageway 158 is substantially cylindrical and extends through body 142 to a third interior cavity, as will be discussed. Second inner surface 156 includes an internal thread form 162 configured for engagement with a coupling member, as will be discussed.

Second passageway 158 defines a second axis, such as, for example, axis a12 disposed at an angular orientation, such as, for example, an angle α1 relative to axis a11. Second passageway 158 is configured for disposal of a coupling member, such as, for example, a set screw 164. Set screw 164 defines a central axis c2, which is disposed in a co-axial alignment with axis a12 upon disposal of set screw 164 with second passageway 158. Set screw 164 has a tubular body that includes an outer surface 166 and an inner surface 168.

Outer surface 166 includes a thread form 170 formed circumferentially about a distal end 172. Thread form 170 threadably engages thread form 162 such that application of torque to set screw 164 causes set screw 164 to translate axially along axis a12. Inner surface 168 receives a driving tool that applies a rotary driving force to set screw 164 for engagement with inner surface 168.

Set screw 164 includes a tapered tip 176 including a concave outer surface 178 disposed circumferentially thereabout. Concave surface 178 is configured for engagement with outer surface 34 to drive spinal rod 32, described above, into engagement with tether 22.

Body 142 includes a third inner surface 180 that defines a third cavity, such as, for example, a third passageway 182. Third passageway 182 has a C-shaped configuration and extends through body 142. Third passageway 182 includes an open end configured for disposing and/or loading spinal rod 32 with body 142. Third passageway 182 defines a third axis, such as, for example, axis a13 disposed in a transverse orientation relative to axis a11 and axis a12. First passageway 148 intersects with third passageway 182 such that first passageway 148 communicates with third passageway 182. Second passageway 158 intersects with third passageway 182 such that second passageway 158 communicates with third passageway 182.

Third passageway 182 is configured for disposal of spinal rod 32 such that connector 140 can be mounted with spinal rod 32, according to the requirements of a particular application. Third inner surface 180 includes a projection 188 configured to engage spinal rod 32 in a provisional locking orientation, similar to that described above.

In operation, spinal rod 32 is disposed in the first configuration (described above with regard to FIGS. 3-5 for example) such that projection 188 engages spinal rod 32 with a resistance to maintain a provisional locking orientation between connector 140 and spinal rod 32. A driving tool applies torque to set screw 164 such that set screw 164 translates axially along axis a12 and concave surface 178 engages outer surface 34. Such engagement overcomes the resistance of projection 188 and spinal rod 32 translates laterally within third passageway 182 such that spinal rod 32 moves from the first configuration to the second configuration (described above with regard to FIG. 6 for example) such that spinal rod 32 translates into engagement with tether 22 for fixation therewith. In one embodiment, connector 140 includes open end 184, which is configured to facilitate passage of an existing rod, disposed within a body of a patient, into third passageway 182 for disposing and/or loading the existing rod with body 142. In one embodiment, the open end of connector 140 is configured to allow connection for placement and/or mounting of the components of spinal correction system 20, such as, for example, tether(s) and/or connector(s) with a previously implanted and/or existing vertebral construct such as, for example, a spinal rod with a body of a patient.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:
1. A spinal correction system comprising:
a plurality of tethers including a first flexible tether;
a spinal rod defining a central axis and including an arcuate outer surface; and
a plurality of connectors including a first connector comprising a body including an outer surface and a first inner surface defining a first passageway extending through the body, the first passageway defining a first axis and being configured for disposal of the first flexible tether, the body further including a second threaded inner surface defining a second passageway extending through the body, the second passageway defining a second axis disposed at an angular orientation relative to the first axis and being configured for disposal of a set screw, the set screw defining a central axis and a tapered tip, and the body further including a third surface defining a third passageway having an oblong cross section extending through the body, the third passageway defining a third axis disposed in a transverse orientation relative to the first axis and the second axis, the third passageway being configured for disposal of the spinal rod, wherein the second passageway communicates with the third passageway such that the tapered tip is engageable with the arcuate outer surface to translate the spinal rod laterally along the oblong cross section of the third passageway and the first passageway communicates with the third passageway such that the spinal rod is engageable with the first flexible tether for fixation therewith.

2. A system as recited in claim 1, wherein the third surface includes a projection configured to engage the spinal rod in a provisional locking orientation.

3. A system as recited in claim 2, wherein the spinal rod is disposable between a first configuration such that the projection engages the second implant with a resistance to maintain the provisional locking orientation and a second configuration such that the engagement of the tapered tip with the arcuate outer surface overcomes the resistance to permit axial translation of the spinal rod along the oblong cross section into engagement with the first flexible tether for fixation therewith.

4. A system as recited in claim 1, further comprising a second connector configured for disposal of a second flexible tether, separate from the first flexible tether, and the spinal rod, the second connector being spaced apart from the first connector along the spinal rod.

5. A method for treating a spine disorder, the method comprising the steps of:
   providing a first flexible implant; disposing the first flexible implant with a first vertebra;
   providing a first connector comprising:
      a first surface defining a first cavity,
      a second surface defining a second cavity configured for disposal of a coupling member, and
      a third surface defining a third transverse cavity and including a projection;
   providing a second implant;
   disposing the second implant with the third cavity such that the projection engages the second implant in a provisional locking orientation;
   disposing the first flexible implant with the first cavity;
   engaging the coupling member with the second implant to overcome the provisional locking orientation of the projection such that the second implant engages the first flexible implant for fixation therewith.

6. A method as recited in claim 5, wherein the step of disposing the first flexible implant with the first vertebra includes disposing the first flexible implant about a transverse process of the first vertebra.

\* \* \* \* \*